(12) United States Patent
Ketterer et al.

(10) Patent No.: US 7,089,603 B2
(45) Date of Patent: Aug. 15, 2006

(54) ADJUSTABLE HEADBAND

(75) Inventors: Kevin R. Ketterer, Portersville, PA (US); Gregoire B. Aby-Eva, Pittsburgh, PA (US); F. Joseph Hersick, Zelienople, PA (US); Paul A. Zeller, Pittsburgh, PA (US)

(73) Assignee: Mine Safety Appliances Company, Pittsburgh, PA (US)

( * ) Notice: Subject to any disclaimer, the term of this patent is extended or adjusted under 35 U.S.C. 154(b) by 0 days.

(21) Appl. No.: 10/988,670

(22) Filed: Nov. 15, 2004

(65) Prior Publication Data

US 2006/0053532 A1      Mar. 16, 2006

Related U.S. Application Data

(60) Provisional application No. 60/610,134, filed on Sep. 15, 2004.

(51) Int. Cl.
*A42B 1/22* (2006.01)
(52) U.S. Cl. .................... 2/418; 2/DIG. 11; 24/DIG. 48
(58) Field of Classification Search ............ 24/593.11, 24/DIG. 48, 68 E, DIG. 45, 272, 663, 664, 24/274 WB, 616, 170, 615, 589.1, 171, 613, 24/593.1, 578.15, 639, 647, DIG. 43, 579.09, 24/DIG. 47; 2/417, 418, 8, DIG. 11, 420, 2/183, 416; 132/59
See application file for complete search history.

(56) References Cited

U.S. PATENT DOCUMENTS

| 3,500,474 | A | * | 3/1970 | Austin | .......................... | 2/418 |
|---|---|---|---|---|---|---|
| 3,992,720 | A | * | 11/1976 | Nicolinas | .......................... | 2/418 |
| 4,844,214 | A | * | 7/1989 | Castelli et al. | .............. | 190/103 |
| 4,942,628 | A | | 7/1990 | Freund | | |
| 5,184,352 | A | * | 2/1993 | Maufette | ................. | 24/579.09 |
| 5,400,484 | A | * | 3/1995 | Gay | ........................ | 24/593.11 |
| 5,896,586 | A | | 4/1999 | Freund | | |
| 6,219,851 | B1 | * | 4/2001 | Fang | ............................. | 2/418 |
| 6,332,227 | B1 | * | 12/2001 | Fang | ............................. | 2/418 |
| 6,341,382 | B1 | | 1/2002 | Ryvin | | |
| 2003/0106138 | A1 | | 6/2003 | Guey | | |
| 2005/0210641 | A1 | * | 9/2005 | Giampavolo | ................. | 24/615 |
| 2005/0262618 | A1 | * | 12/2005 | Musal | ........................... | 2/417 |

FOREIGN PATENT DOCUMENTS

EP      1 074 195      2/2001

* cited by examiner

*Primary Examiner*—Rodney Lindsey
(74) *Attorney, Agent, or Firm*—James G. Uber; Henry E. Bartony, Jr.

(57) ABSTRACT

A headband for use in a headgear support includes a first end section having a plurality of connectors extending latitudinally from a lateral surface of the first end section. The headband also includes a second end section having a fastener attached adjacent the end thereof. The fastener includes a flexible lever arm and a cooperating connector biased in an engagement position with at least one of the plurality of connectors of the first end section to hold the headband in a selected loop configuration. The flexible lever arm is movable to a release position upon application of force thereto to cause the cooperating connector to disengage from the at least one the plurality of connectors of the first end section to enable increasing the size of the loop of the headband. The plurality of connectors of the first end section can, for example, be ratchet teeth.

18 Claims, 8 Drawing Sheets

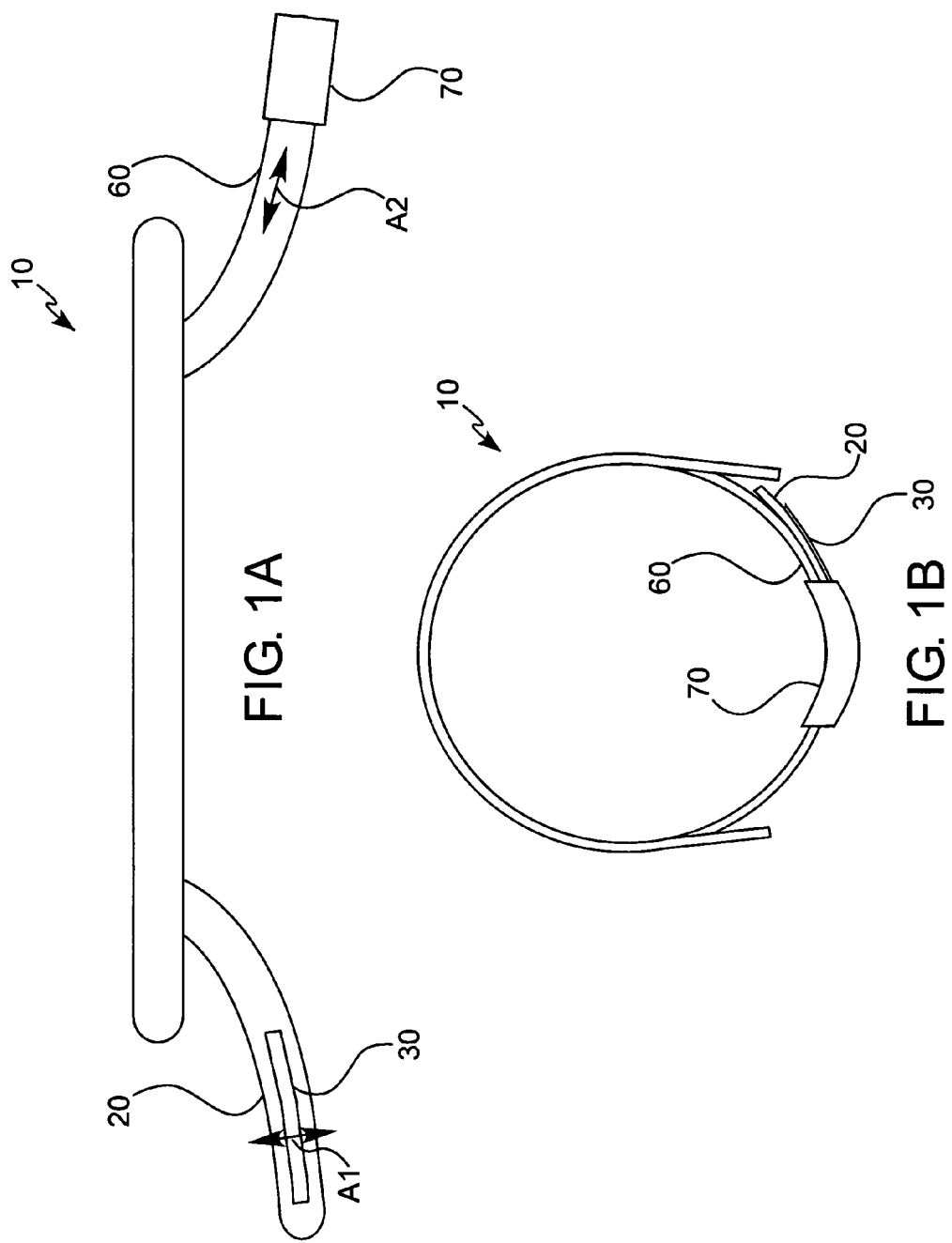

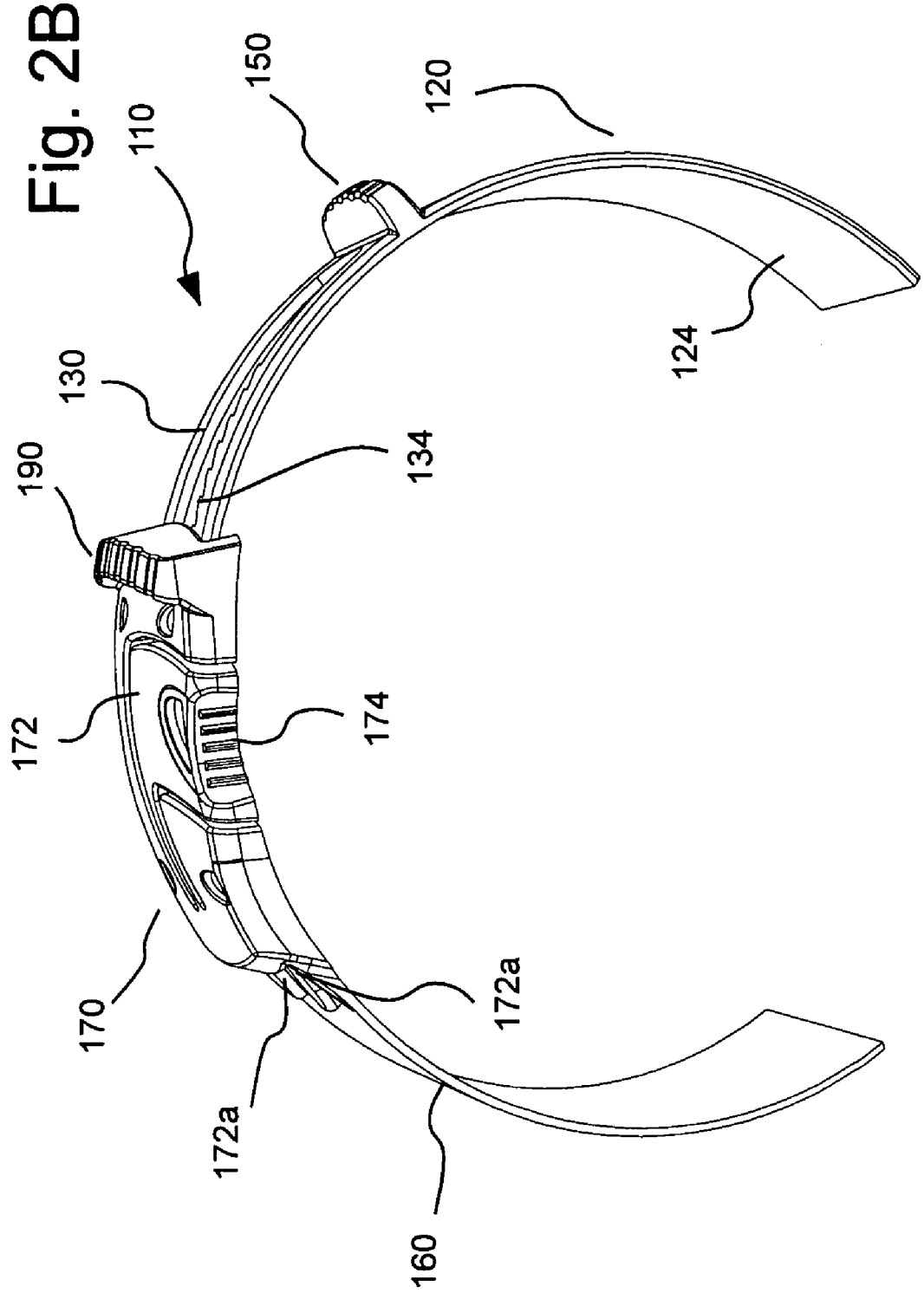

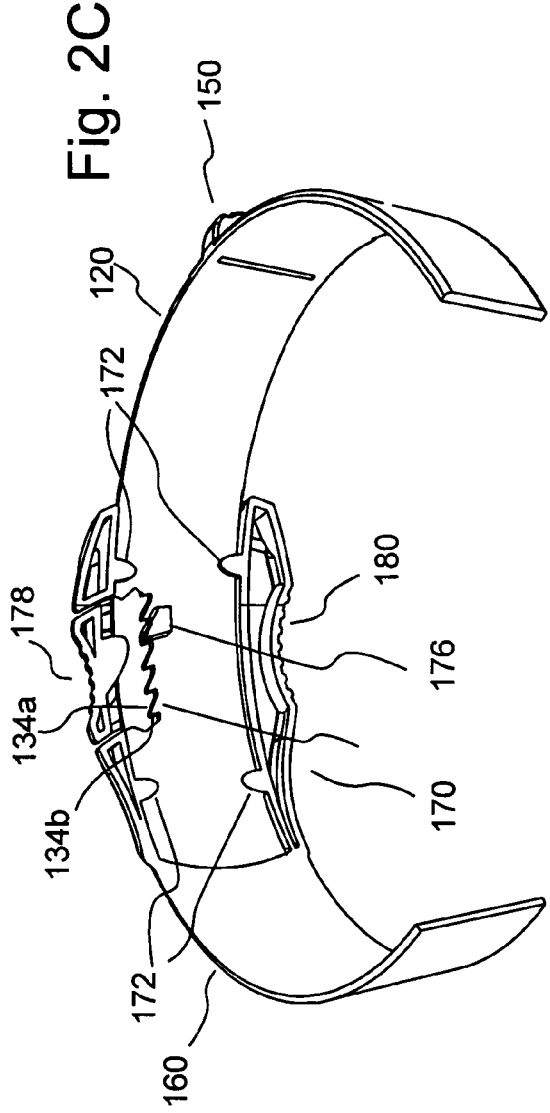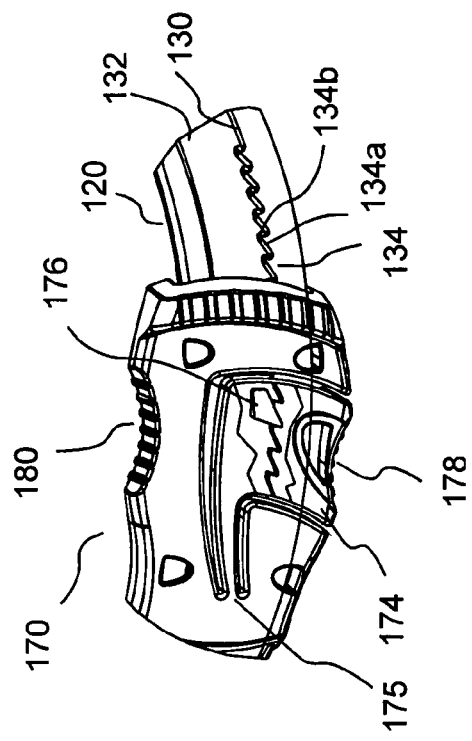

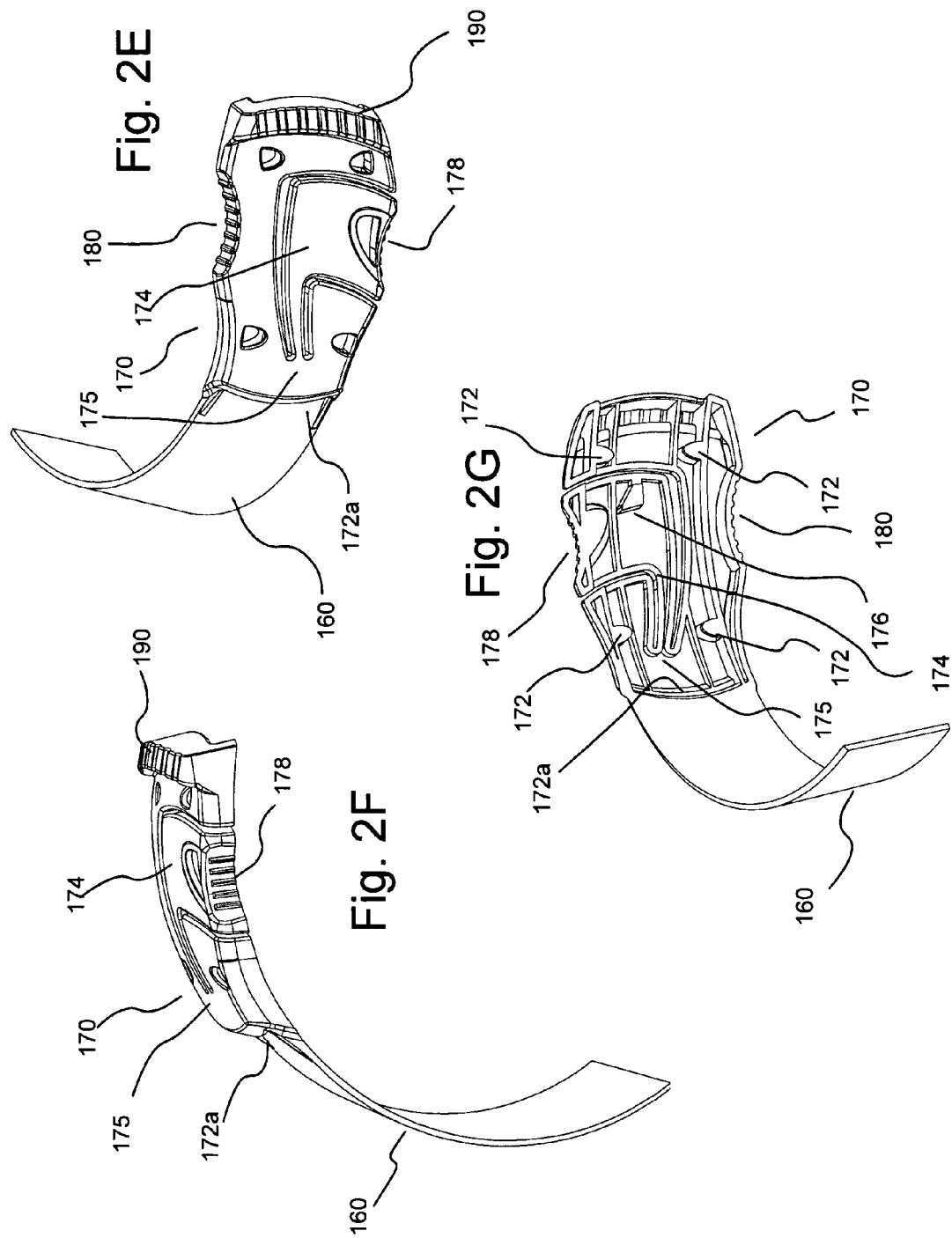

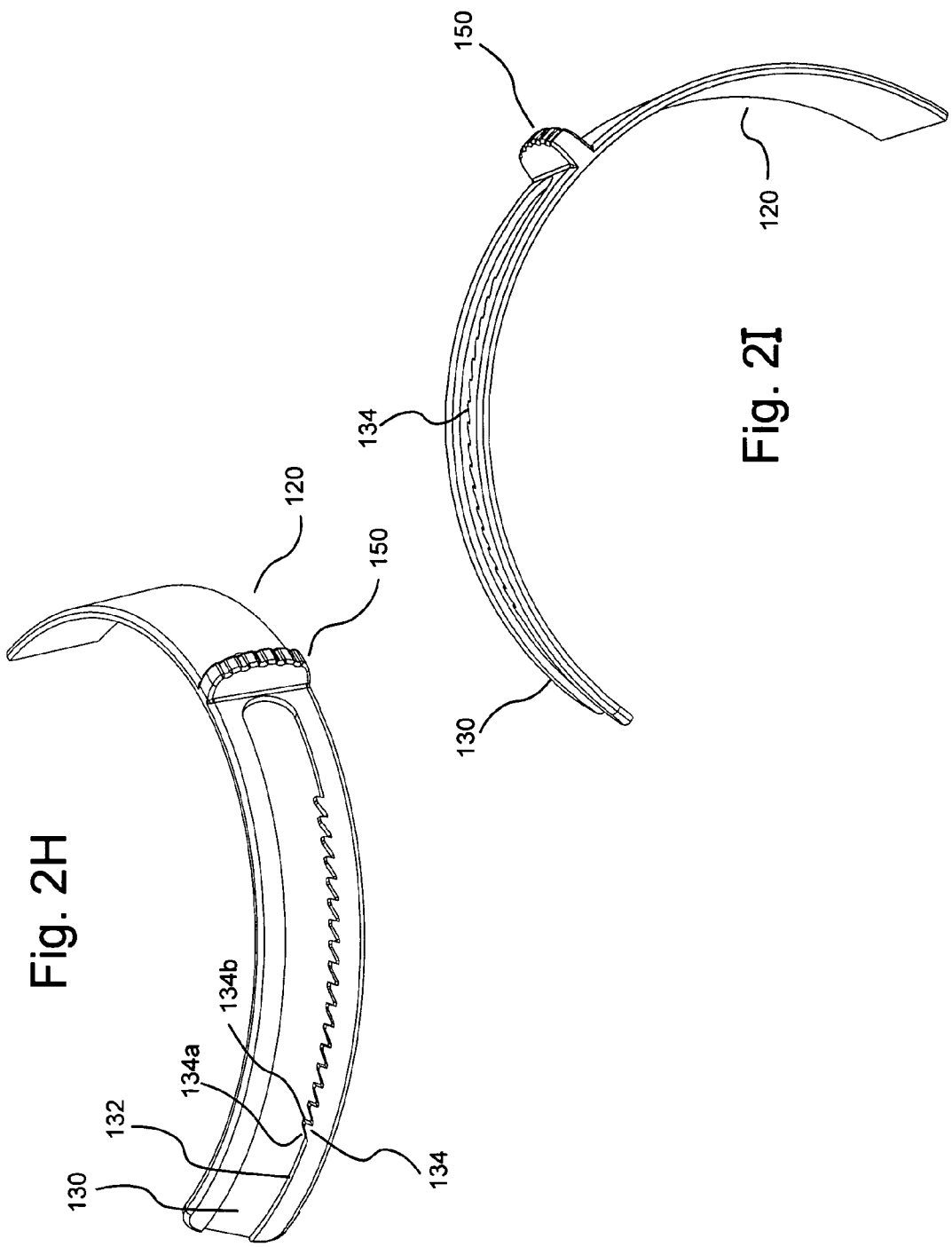

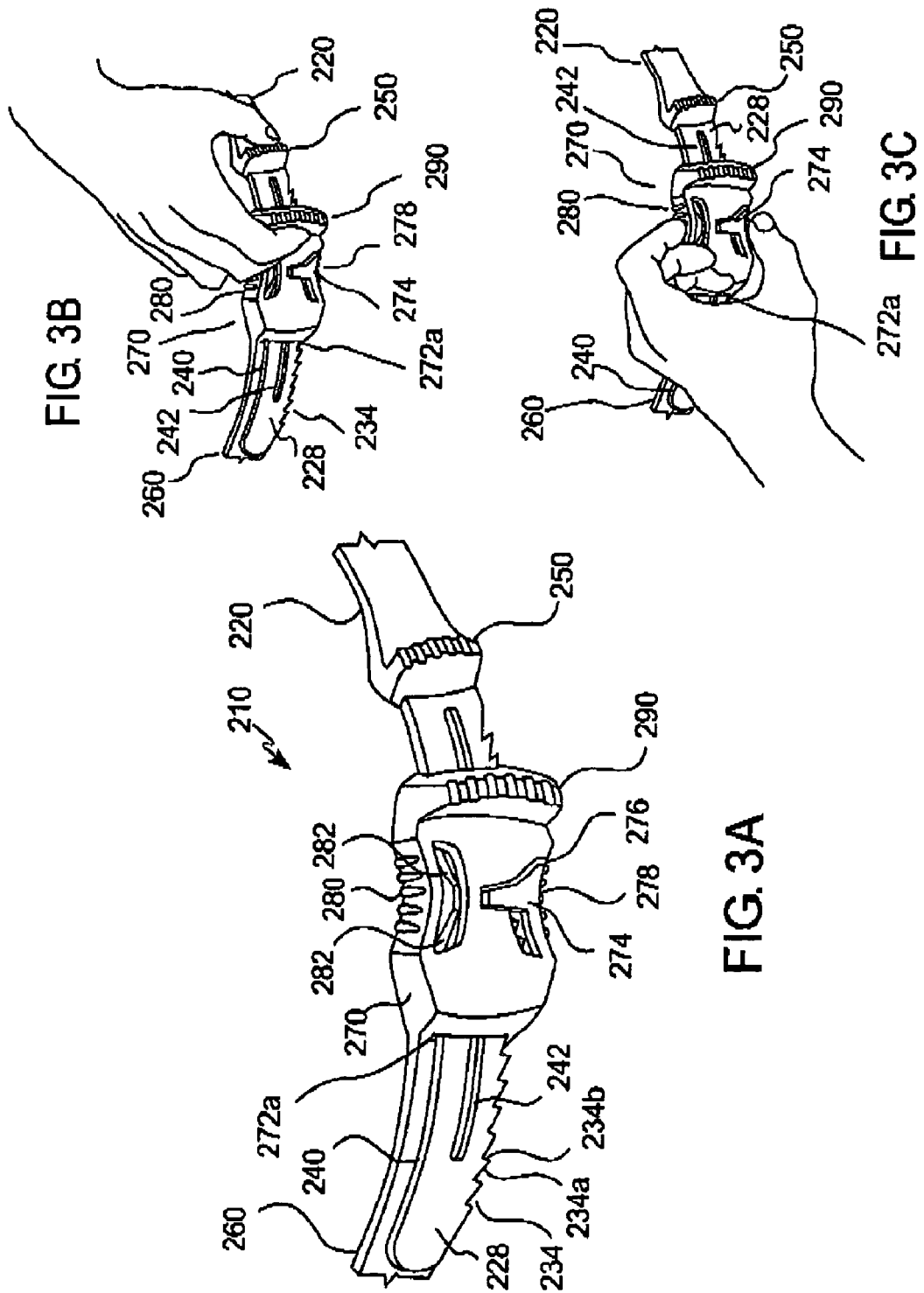

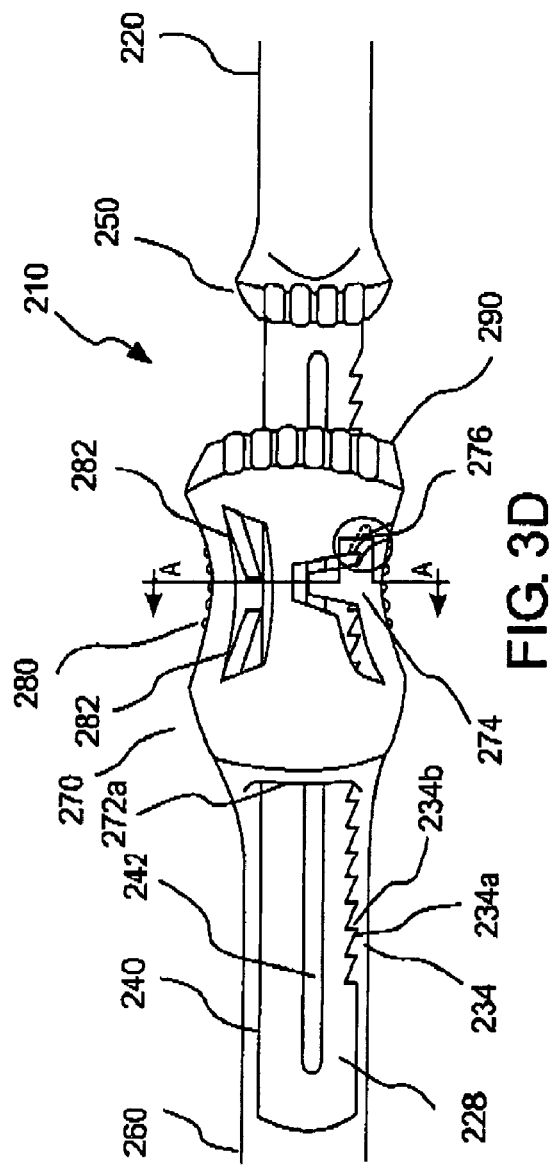
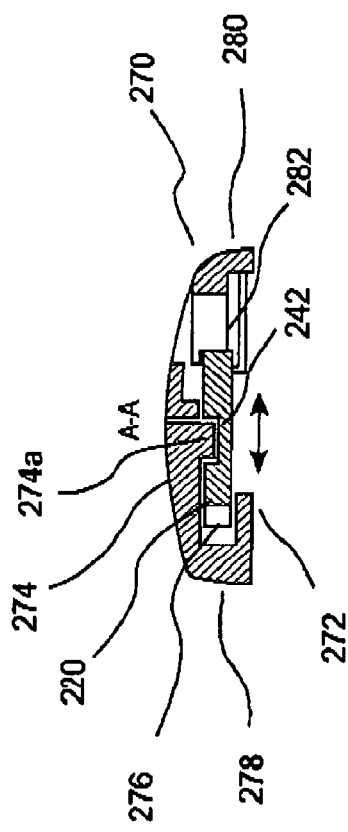
FIG. 3D
FIG. 3E

ADJUSTABLE HEADBAND

CROSS-REFERENCE TO RELATED APPLICATION

This application claims the benefit of U.S. Provisional Patent Application Ser. No. 60/610,134, filed Sep. 15, 2004, the disclosure of which is incorporated herein by reference.

FIELD OF THE INVENTION

The present invention relates generally to adjustable headbands and, particularly, to adjustable headbands for use in headgear, including, for example, personal protective products such as protective helmets, faceshields and welding shields.

BACKGROUND OF THE INVENTION

Most types of protective helmets worn by workers to protect them from falling objects have a suspension system. The suspension system or headgear support, along with the helmet shell, act to absorb the shock of a falling object striking the top of the worker's head. The suspension system also serves as a support that holds the helmet or faceshield on the worker's head.

The suspension is often a web-like support system comprising two or more strips of material that are arranged to cross each other. The ends of the strips are, for example, attached at four or more points around the circumference of the helmet. A headband is then typically attached to the four or more points of the suspension to permit the helmet to be worn by the worker. To securely position the helmet on the worker's head, it is essential that the circumference of the headband be adjustable to fit the appropriate head size. An adjustable napestrap is often attached at one end of the headband to achieve these results. Such a suspension system is available from Mine Safety Appliances Company of Pittsburgh, Pa. under the trademark STAZ-ON®.

U.S. Pat. No. 3,500,474, the disclosure of which is incorporated herein by reference, discloses a headband wherein the napestrap position of the headband is manually adjusted by the wearer to fit the appropriate head size. The two ends of the headband are connected and held in place by a slot-and-projection arrangement. One end of the headband is formed with parallel rows of projections or flanges. The other end of the headband is formed with parallel rows of slots. The size of the headband can be adjusted by inserting the projections of one end of the strap into the slots formed in the other end of the strap at the desired length. Although this type of headband is relatively simple in design and manufacture (in part because separate mechanical fasteners or adjustment mechanisms are generally not required), users of such bands often have difficulty adjusting the band size while wearing the suspension. This inconvenience often results in the use of a different, more expensive type of suspension, such as a ratchet-type suspension system as, for example, described in U.S. Pat. No. 4,942,628.

U.S. Pat. No. 5,896,586, the disclosure of which is incorporated herein by reference, discloses a headband that is relatively simple and inexpensive to manufacture, while providing a fastening mechanism that is relatively easy to adjust. The headband can be fabricated from an integral or monolithic piece of polymeric material. That headband includes a first end and a second end which overlap. The first end includes a plurality of longitudinally spaced attachment members (for example, depressions, recesses or slots). The second end includes a resilient fastener having an opening or a channel to slidably receive the first end in overlapping engagement with the second end. The fastener also includes a fastener surface having at least one cooperating attachment member to cooperate with the attachment members of the first end of the band. The fastener surface is resiliently bowable in a direction away from the first end upon application of a compressive force to the fastener. Upon application of such compressive force, the attachment member of the first end of the band and the cooperating attachment member of the fastener disconnect so that the first end can be slid relative to the fastener (and thereby the second end). Unfortunately, it can be difficult to operate the bowable fastening mechanism of U.S. Pat. No. 5,896,586 with only one hand.

U.S. Pat. No. 6,341,382 also discloses a one-piece adjustable headband which is constructed of lightweight material such as a plastic. The strap is constructed with an integral adjustment or fastening mechanism to adjust the fit of the strap around the head of wearer, purportedly using a single hand. The headband includes a first end, a second end, an interior surface, and an exterior surface. A plurality of ratchet teeth extend from the exterior surface of the headband adjacent the first end thereof. Each of the ratchet teeth has a tapered surface and a locking surface. A clasp is resiliently connected to the exterior surface of the headband adjacent the second end thereof. The clasp includes a pawl which is biased in a locking position wherein the pawl is engageable with the locking surface of one of the ratchet teeth to hold the headband in a selected loop configuration. The clasp is movable to a release position upon application of a force generally normal to the plane of the headband whereby the pawl is moved away from the ratchet teeth to permit the loop configuration of the headband to be increased in size.

Although a number of fastening or adjusting mechanisms have been developed for headbands or head straps for use in headgear, and especially in personal protective equipment such as protective helmets, faceshields and welding shields having a headgear support, it remains desirable to develop improved headbands and adjusting mechanism for use therein, particularly ones which can be adjusted using only one hand, and preferably which can also be adjusted while a user is wearing the protective headgear support.

SUMMARY OF THE INVENTION

In one aspect, the present invention provides a headband for use in a headgear support including a first end section having a plurality of connectors extending latitudinally from a lateral surface of the first end section. The headband also includes a second end section having a fastener attached adjacent the end thereof. The fastener includes a flexible lever arm and a cooperating connector biased in an engagement position with at least one of the plurality of connectors of the first end section to hold the headband in a selected loop configuration. The flexible lever arm is movable to a release position upon application of force thereto to cause the cooperating connector to disengage from the at least one the plurality of connectors of the first end section to enable increasing the size of the loop of the headband. The plurality of connectors of the first end section can, for example, be ratchet teeth.

In one embodiment, the first end section includes a longitudinally extending slot formed therein. The plurality of connectors of the first end section can, for example, extend generally latitudinally from one of the lateral sides of the extending slot. The plurality of connectors of the first end section can also extend generally latitudinally from at least one of a first lateral side and a second lateral side of the first end section.

The cooperating connector can be attached to the flexible lever arm. The lever arm can also be in operative connection with the first end section such that movement of the lever arm to the release position causes movement of the first end section relative to the cooperating connector to disengage the cooperating connector from the at least one of the plurality of connectors on the first end section.

The longitudinally extending slot can pass through the entire depth of the first end section to form an opening therein. Alternatively, the longitudinally extending slot passes only partially through the depth of the first end section.

In another aspect, the present invention provides a headband for use in a headgear support including a first end section having a generally longitudinally extending slot formed therein and a plurality of connectors extending latitudinally from an exterior lateral surface of the first end section. The headband also includes a second end section including a fastener attached adjacent the end thereof. The fastener includes a flexible lever arm and a cooperating connector biased in an engagement position with at least one of the plurality of connectors of the first end section to hold the headband in a selected loop configuration. The flexible lever arm is movable to a release position upon application of force thereto to cause the cooperating connector to disengage from the at least one the plurality of connectors of the first end section to enable increasing the size of the loop of the headband. The plurality of connectors of the first end section can, for example, be ratchet teeth.

The headband can include a projection connected to the fastener which projects into the slot. The cooperating connector can be mounted on the flexible lever arm. In one embodiment, the lever arm is in operative connection with the first end section such that movement of the lever arm to the release position causes movement of the first end section relative to the cooperating connector to disengage the cooperating connector from the at least one of the plurality of connectors on the first end section.

In several embodiments of the headbands of the present invention, a generally latitudinal force is applied to the lever arm to move the lever arm to a release position. As opposed to certain currently available headbands in which a generally normal force is applied to a portion of the headband to cause the headband to enter a release or loosening state, application of a lateral force can be easier, more convenient and/or more ergonomic for a user. Moreover, requirement of application of a latitudinal force can reduce the likelihood of accidentally loosening the headband.

The headbands of the present invention, including the fastener thereof, are readily constructed to have a relatively low profile (that is, the amount the headband extends away from the head in a direction generally normal to the head and to the plane of the headband) as compared to a number of currently available headbands. Such a low profile can reduce the likelihood that the headband will catch on an object in the vicinity of the user. Moreover, such a relatively low profile can also reduce the likelihood of accidental loosening of the headband.

BRIEF DESCRIPTION OF THE DRAWINGS

FIG. 1A illustrates a front plan view of a general embodiment of a headband of the present invention laid flat with the first end section and the second end section disconnected.

FIG. 1B is a top view of the headband of FIG. 1A wherein the first end section and the second end section are connected to form a loop.

FIG. 2B illustrates a side perspective view of the headband of FIG. 2A.

FIG. 2C illustrates a perspective, partially cutaway view of the headband of FIG. 2A.

FIG. 2D illustrates another perspective, partially cutaway view of the headband of FIG. 2A.

FIG. 2E illustrates a front perspective view of the second end section and fastener of the headband of FIG. 2A.

FIG. 2F illustrates a side perspective view of the second end section and fastener of the headband of FIG. 2A.

FIG. 2G illustrates a rear perspective view of the second end section and fastener of the headband of FIG. 2A.

FIG. 2H illustrates a front perspective view of the first end section of the headband of FIG. 2A.

FIG. 2I illustrates a side perspective view of the first end section of the headband of FIG. 2A.

FIG. 3A illustrates a front perspective view of another embodiment of a headband of the present invention wherein the first end section and the second end section are connected.

FIG. 3B illustrates tightening of the fit the headband of FIG. 3A.

FIG. 3C illustrates application of force to a lever arm of the fastener of the headband of FIG. 3A to loosen the fit of the headband.

FIG. 3D illustrates a front plan view of the headband of FIG. 3A.

FIG. 3E illustrates a cross-sectional view of the headband of FIG. 3A.

DETAILED DESCRIPTION OF THE INVENTION

Figure 2A:
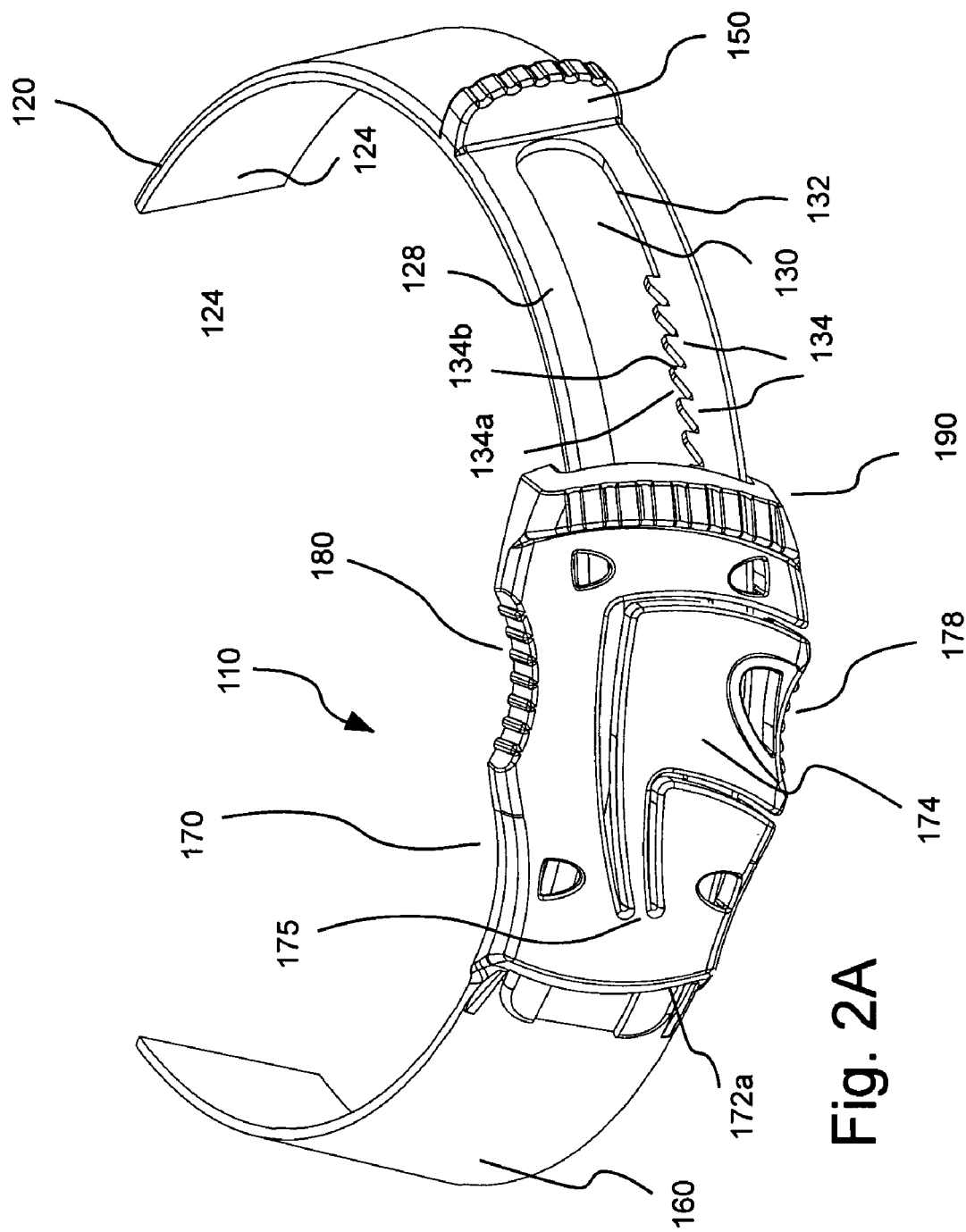
FIG. 2A illustrates a front perspective view of one embodiment of a headband of the present invention wherein the first end section and the second end section are connected.

FIGS. 1A and 1B illustrate the general design of a headband or head strap 10 of the present invention for use in a headgear support. Headband 10 is, for example, a flexible member that can be molded from one or more suitable polymeric materials to extend around the head of the user. Headband 10 can, for example, be formed from an integral or monolithic piece of polymeric material or can, for example, be co-molded or otherwise fabricated from two or more polymeric materials. A first end 20 and second end 60 overlap at the back of the wearer's head. Headband 10 may be straight from end to end, in which case first end 20 and second end 60 will overlap on the head of the user. On the other hand, first end 20 and second end 60 may extend downwardly in the rear portion of headband 10 across the nape of the neck. The latter embodiment is illustrated in FIGS. 1A and 1B. Regardless of which type of headband 10 is used, overlapping ends 20 and 60 are connected in the same manner.

First end 20 includes a connection mechanism 30 that typically comprises a plurality of longitudinally spaced connective elements. Second end 60 includes a cooperating fastener 70 which includes at least one cooperating connective element that forms an operative connection with at least one of the spaced connective elements of connection mechanism 30 to form an adjustable overlapping connection between first end 20 and second end 60. In the embodiments described below, only the section of the headband including the fastening or adjusting mechanism is illustrated in the corresponding drawings. Reference can be made to FIGS. 1A and 1B for an embodiment of the headgear support. In FIG. 1A, arrow A1 represents a generally latitudinal direction as such term is used herein, whereas arrow A2 represents a generally longitudinal direction as such term is used herein.

FIGS. 2A through 2C illustrate one embodiment of a headband 110 of the present invention including a first band end section or end 120 and a second band end section or end 160. First end 120 includes a rear surface 124 and a forward surface 128. First end 120 also includes an extending slot 130 formed in the forward surface thereof. Extending slot 130 can be formed to pass through the entire depth or thickness of first end 120 to form a passage therethrough. In the embodiment of FIGS. 2A through 2C, however, extending slot 130 is of a depth not to pass through to rear surface 124. Forming slot 130 to a depth only partially through first end 120 provides for a smoother rear surface 124, which can facilitate movement of first end 120 relative to second end 160 and reduce the likelihood of catching a wearer's hair. A plurality of connective elements in the form of ratchet teeth 134 are formed on at least one side or lateral surface 132 of extending slot 130. Ratchet teeth 134 thus extend in a latitudinal direction, parallel to forward or front surface 128 and rear surface 124.

Second end 160 includes fastener 170 at the end thereof. First end 120 is maintained in slidable connection with fastener 170 and second end 160 via retaining members 172 (see, for example, FIG. 2G) on the interior of fastener 170. First end 120 also passes through an opening 172a formed in fastener 170. Retaining members 172 and opening 172a form a channel through which first end 120 is slidable to adjust the loop formed by headband 110 (see, for example, FIG. 1B for an example of the loop configuration). Fastener 170 includes a flexible lever arm 174 having an abutment member or tooth 176 (see FIGS. 2C and 2F) attached thereto. Abutment member 176 extends into slot 130 to form an operative connection with one of teeth 134 (see FIGS. 2C and 2D). Lever arm 174 and the remainder of fastener 170 can, for example, be fabricated (via, for example, molding) from a resilient polymeric material wherein lever arm 174 flexes about an attachment point 175 relative to the remainder of fastener 170. Lever arm 174 biases abutment member 176 in operative connection with ratchet teeth 134 of first end 120.

In the embodiment of FIGS. 2A through 2I, ratchet teeth 134 include a first surface 134a proximal to or facing second end 160, that is sloped to facilitate sliding of first end 120 through fastener 170 to reduce the size of headband 110 (thereby tightening the fit thereof). For example, application of an appropriate force to first end 120 (and/or second end 160) to tighten headband 110 causes abutment member 176 to "ride over" sloped surfaces 134a of ratchet teeth 134. Ratchet teeth 134 further include a second or locking surface 134b distal from or facing away from second end 160 that is generally vertical. Surface 134b, in cooperative connection with abutment member 176, provides substantial resistance to movement of first end 120 away from second end 160 (which would result in loosening of the fit of headband 110). In that regard, loosening of the fit of headband 170 typically requires application of a generally latitudinal force to flexible lever arm 174 to move abutment member 176 out of operative abutment with ratchet teeth 134. In the embodiment of FIGS. 2A through 2I, the wearer of headband 110 can apply upward latitudinal force (in the orientation of FIG. 2A) to flexible lever arm 174 at finger rest or contact 178. A second finger rest or contact 180 can be provided opposite of finger rest 178 to facilitate grasping of fastener 170 by the wearer and application of force to flexible lever arm 178. In that regard, the user can readily reach behind his or her head while wearing headgear support incorporating headband 110, place the user's thumb on contact 178 and the user's index finger on contact 180, and apply sufficient force to flexible lever arm 174 to remove abutment member 176 from operative contact with ratchet teeth 174 to loosen the fit of headband 110. Likewise, the user can readily reach behind his or her head, place the user's fingers in contact with tab 150 on first end 120 and with tab 190 on fastener 170, and force tabs 150 and 190 toward each other to tighten the fit of headband 110.

FIGS. 3A through 3E illustrate another embodiment of a headband 210 of the present invention which, in a number of respects, operates in a similar manner to headband 110. Headband 210 includes a first end 220 and a second end 260. First end 220 includes a series of ratchet teeth 234 which project in a generally latitudinal direction from a lower (in the orientation of FIG. 3A) lateral surface 236 of first end 220. Like ratchet teeth 134, ratchet teeth 234 include a sloped surface 234a and a generally vertical locking surface 234b, which facilitates tightening of headband 210, but causes substantial resistance to the loosening thereof.

Second end 260 includes a fastener 270. Similarly to fastener 170, fastener 270 includes tabs 272 (see FIG. 3E) on a rearward side thereof and an opening 272a (see, for example, FIG. 3A) which assist in maintaining first end 220 in slidable operative connection with fastener 270 and second end 260. Fastener 270 further includes a flexible lever arm 274 (for example, formed integrally therewith) which is in operative connection with a slot 242 formed in a forward surface 228 of first end 220 via a projection or a pin 274a (see FIG. 3E). Ratchet teeth 234 are biased into contact with an abut member 276 (see FIG. 3D) fixed to fastener 270, via flexible lever arms 282 which abut an upper, lateral surface 240 of first member 220. When a latitudinal force (an upward latitudinal force in the orientation of FIGS. 3C and 3D) is applied to lever arm 274, the operative connection of pin 274a with slot 242, forces first end 220 upward relative to second end 260 and removes ratchet teeth 234 from operative contact with abutment member 276. Finger contacts 278 and 280 can be used in the manner described above in connection with finger contacts 178 and 180 to facilitate loosening of headband 210. Likewise, tabs 250 and 290 can be used in the manner described above in connection with tabs 150 and 190 to facilitate tightening of headband 210.

The foregoing description and accompanying drawings set forth preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A headband for use in a headgear support, comprising:
   a first end section comprising a plurality of connectors extending latitudinally from a lateral surface of the first end section and a first abutment member extending outwardly from the first end section; and
   a second end section comprising a fastener attached adjacent the end thereof, the fastener comprising a first end and a second end and second abutment member adjacent the first end of the fastener and extending outwardly from the fastener the fastener further comprising a flexible lever arm positioned between the first end and the second end and a cooperating connector biased in an engagement position with at least one of the plurality of connectors of the first end section to hold the headband in a selected loop configuration, the flexible lever arm being movable to a release position upon application of force thereto to cause the cooperating connector to disengage from the at least one the plurality of connectors of the first end section to enable increasing the size of the loop of the headband, the first abutment member of the first and section end the second abutment member of the second section being adapted to be contacted by a user's fingers to be moved toward each other to decrease the circumference of the headband.

2. The headband of claim 1 wherein the first end section comprises a longitudinally extending slot farmed therein, the plurality of connectors of the first end section extending generally latitudinally from one of the lateral sides of the extending slot.

3. The headband of claim 2 wherein the plurality of connectors of the first end section are ratchet teeth.

4. The headband of claim 1 wherein the first end section comprises a first lateral side and a second lateral side, the plurality of connectors of the first end section extending generally latitudinally from at least one of the first lateral side and the second lateral side.

5. The headband of claim 4 wherein the plurality of connectors of the first end section are ratchet teeth.

6. The headband of claim 1 wherein the cooperating connector is attached to the flexible lever arm.

7. The headband of claim 1 wherein the lever arm is in operative connection with the first end section such that movement of the lever arm to the release position causes movement of the first end section relative to the cooperating connector to disengage the cooperating connector from the at least one of the plurality of connectors on the first end section.

8. The headband of claim 1 wherein a generally latitudinal force is applied to the lever arm to move the lever arm to a release position.

9. The headband of claim 2 wherein the longitudinally extending slot passes through the entire dept of the first end section to form an opening therein.

10. The headband of claim 2 wherein the longitudinally extending slot does not pass trough the entire depth of the first end section.

11. A headband for use in a headgear support, comprising:
    a first end section comprising a generally longitudinally extending slot formed therein and a plurality of connectors extending latitudinally from an exterior lateral surface of the first end section, the first end further comprising a first abutment member extending outward from the first end section; and
    a second end section comprising a fastener attached adjacent the end thereof, the fastener comprising a first end and a second end and second abutment member adjacent the first end of the fastener and extending outwardly from the fastener, the fastener further comprising a flexible lever arm positioned between the first and second end and a cooperating connector biased in an engagement position with at least one of the plurality of connectors of the first end section to hold the headband in a selected loop configuration, the flexible lever arm being movable to a release position upon application of force thereto to cause the cooperating connector to disengage from the at least one the plurality of connectors of the first end section to enable increasing the size of the loop of the headband, the first abutment member of the first end section and the second abutment member of the second section being adapted to be contacted by a user's fingers to be moved toward each other to decrease the circumference of the headband.

12. The headband of claim 11 wherein the plurality of connectors of the first end section are ratchet teeth.

13. The headband of claim 11 further comprising a projection connected to the fastener which projects into the slot.

14. The headband of claim 11 wherein the cooperating connector is mounted on the flexible lever arm.

15. The headband of claim 11 wherein the lever arm is in operative connection with the first end section such that movement of the lever arm to the release position causes movement of the first end section relative to the cooperating connector to disengage the cooperating connector from the at least one of the plurality of connectors on the first end section.

16. The headband of claim 11 wherein a generally latitudinal force is applied to the lever arm to move the lever arm to a release position.

17. The headband of claim 11 wherein the longitudinally extending slot passes trough the entire depth of the first end section to form an opening therein.

18. The headband of claim 11 wherein the longitudinally extending slot does not pass through the entire depth of the first end section.

* * * * *

UNITED STATES PATENT AND TRADEMARK OFFICE
CERTIFICATE OF CORRECTION

PATENT NO. : 7,089,603 B2  
APPLICATION NO. : 10/988670  
DATED : August 15, 2006  
INVENTOR(S) : Kevin R. Ketterer et al.

Page 1 of 1

It is certified that error appears in the above-identified patent and that said Letters Patent is hereby corrected as shown below:

Column 7,  
Line 22, delete "first and section end" and insert -- first end section and -- therefor.  
Line 28, delete "farmed" and insert -- formed -- therefor.  
Line 54, delete "dept" and insert -- depth -- therefor.

Column 8,  
Line 2, delete "trough" and insert -- through -- therefor.  
Line 23, delete "one the" and insert -- one of the -- therefor.  
Line 49, delete "trough" and insert -- through -- therefor.

Signed and Sealed this

Fourteenth Day of August, 2007

JON W. DUDAS  
*Director of the United States Patent and Trademark Office*